United States Patent [19]
Smolnik et al.

[11] Patent Number: 5,384,035
[45] Date of Patent: Jan. 24, 1995

[54] METHOD FOR PROCESSING INDUSTRIAL DISCHARGES

[75] Inventors: Heinz-Dieter Smolnik, Brunswick; Jürgen Thommel, Wolfenbüttel, both of Germany

[73] Assignee: Amino GmbH, Frellstedt, Germany

[21] Appl. No.: 123,295

[22] Filed: Sep. 17, 1993

[30] Foreign Application Priority Data

Sep. 17, 1992 [DE] Germany .................. 4231149

[51] Int. Cl.⁶ ............................... B01D 15/08
[52] U.S. Cl. .............................. 210/635; 210/656; 127/46.3
[58] Field of Search ............ 210/635, 656, 659, 198.2; 127/46.3, 55

[56] References Cited

U.S. PATENT DOCUMENTS

| | | | |
|---|---|---|---|
| 2,375,165 | 5/1945 | Nees | 260/534 |
| 2,586,295 | 2/1952 | Brown | 260/501 |
| 2,937,959 | 5/1960 | Reents | 127/46 |
| 3,214,293 | 10/1965 | Mountfort | 127/9 |
| 4,359,430 | 11/1982 | Heikkila | 260/501.13 |
| 5,084,104 | 1/1992 | Heikkila | 127/46.3 |
| 5,127,957 | 7/1992 | Heikkila | 17/46.3 |
| 5,176,832 | 1/1993 | Dorta | 210/635 |
| 5,221,478 | 6/1993 | Dhingra | 210/635 |

FOREIGN PATENT DOCUMENTS 54544 6/1982 European Pat. Off. ............ 210/635

*Primary Examiner*—Ernest G. Therkorn
*Attorney, Agent, or Firm*—Herbert Dubno

[57] ABSTRACT

In a method for the further processing of industrial residue discharge from molasses processing, in particular vinasse or residual molasses, employing a separating column with an ion-exclusion method, elution takes place with dilute or back-diluted solution of the starting material.

13 Claims, 2 Drawing Sheets

METHOD FOR PROCESSING INDUSTRIAL DISCHARGES

BACKGROUND OF THE INVENTION

The invention relates to a method for the further processing of industrial residue discharges from molasses processing, for example of vinasse (slop) or residual molasses, by means of ion-exclusion chromatography.

During molasses processing there is obtained as an industrial residue discharge in particular vinasse or slop or residual molasses. Said products have been utilizable only with difficulty to date and their disposal also presents problems.

An initial aim of the invention therefore consists in proposing a method for further processing with which the amounts to be disposed of may be reduced and/or components which are still utilizable economically be obtained.

Betaine, for instance, could be considered as an important component of such industrial residue discharges.

Betaine (($CH_3)_3$—$N^+$—$CH_2$—$COO^-$, $C_5H_{11}NO_2$) occurs in various plant species, but above all in sugar beet. During the obtaining of sugar from sugar beet the betaine accumulates in the molasses; the concentration lies in the range from 3 to 8% betaine in the dry matter.

Also during many biotechnological processes with molasses as raw material (source of carbon), e.g. during the production of yeast or alcohol, betaine is not assimilated and therefore accumulates in the final discharges of said processes, for instance in the vinasse (molasses slop). The betaine concentrations may further-more amount to more than 15% of the dry matter.

Similar concentrations are also found in the residual molasses during processes for the desugarizing of molasses, e.g. according to the barium sulphate or Steffen process.

Because of its property as a methyl group donor, betaine is used mainly as an additive for feedstuffs. In addition, however, betaine is also used in cosmetic and pharmaceutical preparations, for instance as a skin care agent or a liver protection preparation.

Various methods have been developed for the obtaining of betaine. The latter including obtaining by crystallization as hydro-chloride, by extraction with the aid of organic solvents, by ion exchange and in particular by means of ion-exclusion chromatography, as proposed for example in EP 0 054 544 B1.

Said method tested many times in practice for the obtaining of betaine from molasses takes place as follows: A cationic exchanger is loaded with the solution to be processed. In so doing the molasses is diluted to such an extent that it possesses a solids content in the approximate range of 20 to 50%. In the cationic exchanger two effects essentially take place simultaneously side by side, ion exclusion and the molecular sieve effect. The strong electrolytes migrate relatively undisturbed through the separating column, while the weak electrolytes and non-electrolytes are adsorbed by the exchanger. Due to the elution with water the absorbed substances are released again. In addition, due to the different rates of migration through the exchanger, the electrolytes and non-electrolytes are separated from one another, and fractions of different compositions are obtained.

Whereas the diluted molasses is passed as a uniform charge onto the top side of a separating column, the various substances appear in a spaced time sequence after passing through the separating column. Since the components of the original substance are essentially constant and known, it may also be predicted with a high degree of accuracy which components will appear in the outlet of the separating column and when, so that the individual fractions may be deliberately separated from one another.

Although the fractions of the various charges are of constant composition, they may nevertheless be optimized in a suitable manner within certain limits by deliberate choice of the process parameters.

Completely accurate separation of the components is however not possible; there are certain mixed amounts between the individual fractions in each case.

The current methods start from the fact that discharges from sugar beet processing, such as e.g. molasses, are purified by multiple separation according to the ion-exclusion method with water as eluent. The use of water helps to ensure as clean a separation as possible of the individual fractions from one another and keeps the "mixed discharges" relatively small. If other eluents were to be used, additional impurities would also be introduced, and this has therefore been refrained from to date.

Despite the intrinsically good results of the known method it is disadvantageous that high evaporation and processing costs are incurred, since at the outlet of the separating column the individual fractions contain large amounts of water. As a result, the obtaining of the valuable components, in particular betaine, from industrial residue discharges is not always economic. This applies in particular to the processing of vinasse or residual molasses, where a further cost unit is not available as in the case of the obtaining of sugar from molasses.

It is therefore a further aim of the invention to develop the generic method in such a way that a more cost-effective obtaining of betaine is possible also from such residue discharges.

SUMMARY OF THE INVENTION

The above-mentioned aims are achieved by the fact that at least in the first separation pass through the separating column the elution of the substances to be separated takes place with dilute or back-diluted solution of the starting material.

The measure appears contradictory at first sight in view of the stated intention. Due to the use of a solution of the starting product for the elution, the clear gaps between the various fractions which are achieved and aimed at per se in the separating column are "blurred", and are therefore distinguishable less clearly from one another. Due to the elution with precisely the same materials as in fact are to be separated from one another, the appearance of the latter in the outlet is actually extended slightly in time in each case, so that the overlapping areas increase sharply.

The advantage of said at first sight seemingly contradictory measure consists however in the fact that all the fractions appearing in the outlet are substantially enriched. In particular the water content of the fractions appearing drops significantly, so that the subsequent evaporation and processing costs also decrease accordingly.

Due to the resulting higher concentration of the individual fractions it becomes possible, during their correlation which takes place in the time sequence, to delimit the edge zones becoming slightly more uncertain as a result of the blurring, i.e. to dispense in effect with parts of the betaine obtained. Since however the betaine content in the remaining zones has now risen in relation to the dry matter, a higher purity is neverthe-less ensured.

The carrying out of a plurality of separation passes successively of the same substance also had to be carried out in the prior art, in order to ensure a reliable separation and to be able to further process by known methods the products obtained.

It has proved particularly effective in practice if the elution is carried out with dilute or back-diluted solution of the starting material with a concentration between 2 and 12% dry matter, preferably with 5%.

With said concentrations a particularly good balance between the individual effects has been obtained, i.e. the "blurring" of the individual fractions still remains relatively slight, on the other hand a substantial increase in the concentrations already takes place on the whole.

Preferably the first and in certain cases a second separation pass with an elution of the starting material takes place.

Thereafter it is recommended that one or more additional separation passes be carried out with water, which now however take place with a substantially higher initial purity.

Vinasse and other residue discharges from molasses processing contain still further valuable components, for example pyrrol-idone carboxylic acid (glutamic acid). It has scarcely been possible to date, however, to obtain said components of vinasse in an economically utilizable form. There has however been proposed in the subsequently published European patent application 91 104 968.2 a method for the manufacture of a humectant in which precisely these components play an important role.

It is therefore a further aim of the invention to propose a method for the obtaining of amino acids and other organic acids from industrial residue discharges from molasses processing.

Said aim also is achieved by the fact that at least in the first separation pass through a separating column the elution of the substances to be separated takes place with dilute or back-diluted solution of the starting material.

The obtaining of said further, valuable components may even be carried out simultaneously with the method for the obtaining of betaine. Said components will in fact during the ion-exclusion method leave the separating column in a time domain separate from the focal point for betaine.

The fractions obtained during the separation passes may then be subjected to specific further processing. Thus not only betaine, the main product proper, is obtained, but also -aminobutyric acid (GABA), L-aspartic acid, glycine, L-alanine, L-leucine, L-serine, L-valine, L-isoleucine, L-threonine, lactic acid etc. . Moreover there is contained in the vinasse above all L-glutamic acid, which is present in the form of its conversion product as L-pyrrolidone carboxylic acid (PCA). It occurs with the splitting of ammonia by cyclization from L-glutamine.

Polystyrene resins with a divinylbenzne crosslinking of nominally 3 to 7% are highly suitable as cationic exchangers in the separating columns. The active groups are sulphonic acid groups, preferably in sodium form. The particle size of the resins lies between 0.2 and 0.5 mm, a uniform size distribution in particular being of great importance for the separation quality.

There are obtained by the method according to the invention, with the concentrating of the value-giving fractions, solutions of high purity which may either be marketed directly as a concentrated solution or may be used for the obtaining of amino acids and other organic acids and betaine by drying or fractional crystallization.

BRIEF DESCRIPTION OF THE DRAWINGS

Preferred embodiments of the present invention will now be described with reference to the accompanying drawings, of which.

DESCRIPTION OF THE PREFERRED EMBODIMENTS

Basically the invention provides a method for the further processing of industrial residue discharges from molasses processing, with a starting material in particular of vinasse or residual molasses, by means of ion-exclusion chromotography comprising at least a first separation pass through a separating column, wherein during said pass, elution of the substances to be separated takes place with dilute or back-diluted solution of said starting material.

A double-walled separating column 1 with a diameter of 0.1 m is filled with 30 l of cation exchanger resin in sodium form. Through the twin jacket the temperature is brought to approx. 85° C. The resin spherules are saturated with a 5% vinasse solution and irrigated with said 5% vinasse solution until equilibrium is established. Then 4 l of a concentrated vinasse solution (at 11) of approx. 35% DM (feed solution) are fed onto the resin surface. The feed solution is subsequently diluted with 5% vinasse solution (at 12). It must be ensured in this connection that the vinasse solutions have been purified of cloudy and suspended matter in a suitable manner prior to use.

Figure 1:
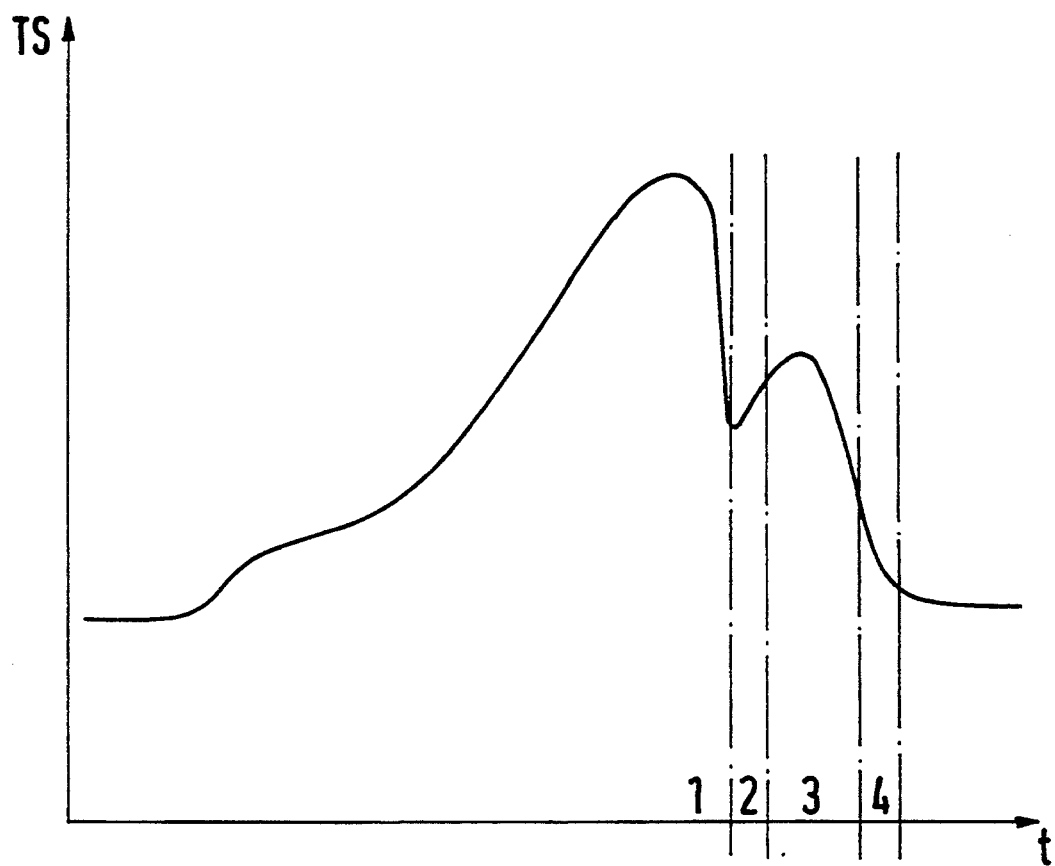
FIG. 1 shows a time plot at the outlet of the separating column; the time is entered on the right and the amount of dry matter DM at the top
Figure 2:
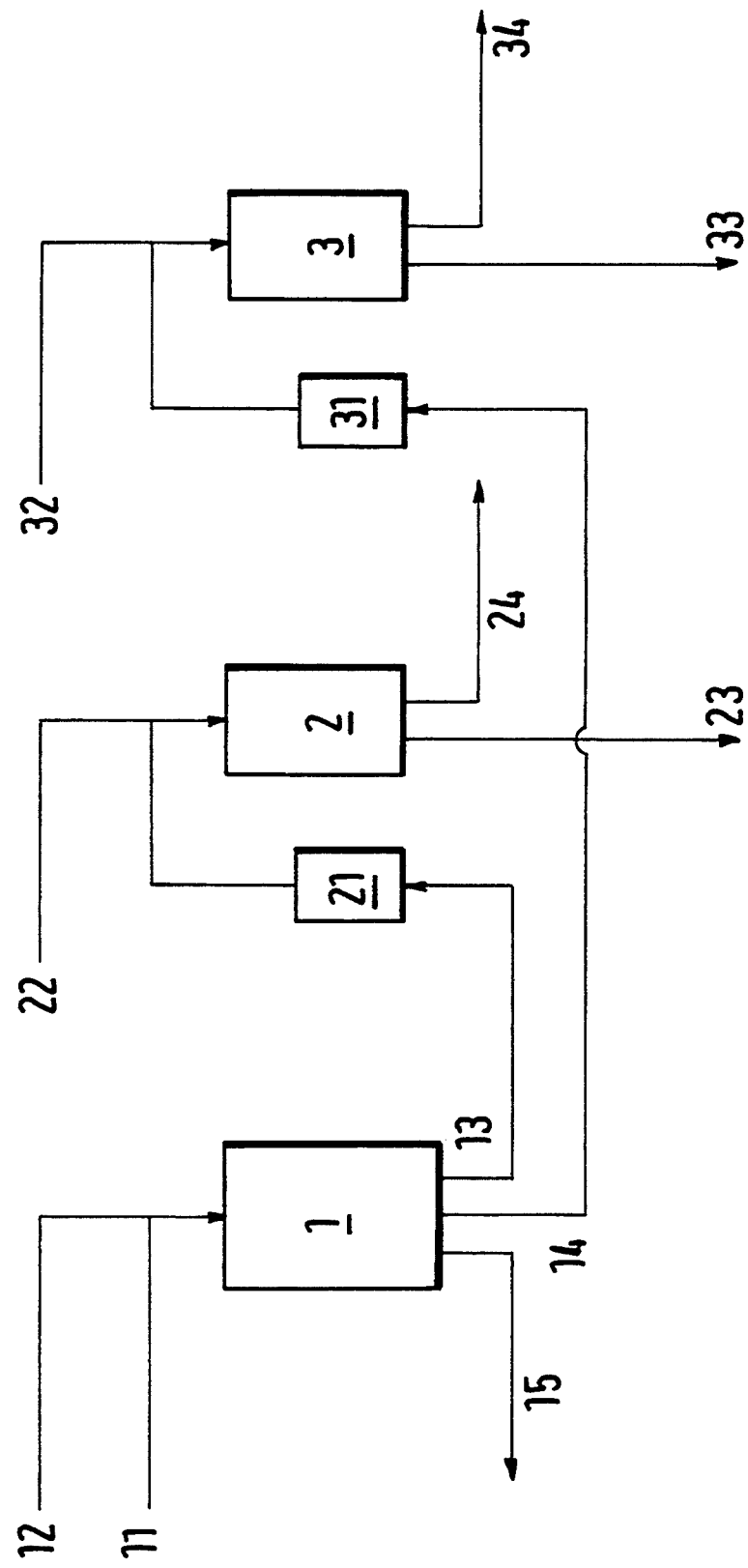
FIG. 2 shows a schematic representation of the steps of the method.

The solutions leaving the separating column 1 are monitored continuously by means of a differential refractometer and a conductivity meter, which records values. With the use of a microprocessor the following fractions may be separated from one another on the basis of the determined density and conductivity values and the run time as parameters (FIG. 1):

1. Salt and amino acid fraction (L-pyrrolidone carboxylic acid) is drawn off for separate processing (at 14 in FIG. 2).
2. Recycling 1 is withdrawn for the feed solution (at 15 in FIG. 2).
3. Betaine fraction (at 13 in FIG. 2).
4. Recycling 2, is recycled for the elution solution (at 15 in FIG. 2).

The betaine fraction (at 13) is collected for further processing. It contains on average some 40% of betaine in the solids. The betaine solution is then evaporated to approx. 35% solids (at 21) and further purified on a further separating column 2 with water (condensate, at 22) as eluent in a second or multiple separation pass. The method correponds to the separation process already described above. The purity of said purified betaine fraction comes to approx. 90% in the solids. Said betaine fraction (at 23) may therefore be marketed either straightway or after evaporation as a concentrated solution, or else the betaine is crystallized by known methods and obtained in high purity and yield. An effluent fraction remains behind (at 24).

The salt and amino acid fraction or fraction of organic acids, which also contains the L-pyrrolidone carboxylic acid, obtained (at 14) is after evaporation (at 31) further purified on a further separating column 3 with water (condensate, at 32) as eluent in a second or multiple separation pass. The concentrated organic acids may now be passed to the following processing stage (at 33); at 34 another effluent fraction is obtained. On completion of a separation pass the next cycle may be started immediately.

It will be understood that the above description of the present invention is susceptible to various modifications, changes and adaptations.

What is claimed is:

1. A method for the further processing of industrial residue discharges from molasses processing, with a starting material of vinasse or residual molasses, by means of ion-exclusion chromotography comprising at least a first separation pass through a separating column, wherein during said pass, elution of the substances to be separated takes place with dilute or diluted solution of said starting material.

2. A method according to claim 1, wherein concentrating of said dilute or diluted solution of said starting material is carried out with a concentration between 2 and 12% dry matter.

3. A method according to claim 1, wherein betaine is obtained from industrial residue discharges from molasses processing.

4. A method according to claim 3, wherein a betaine fraction obtained after said first separation pass is concentrated and eluted again in a second separation pass with dilute or diluted solution of said starting material.

5. A method according to claim 3, wherein a betaine fraction obtained is concentrated and, after said separation with said solution, also eluted and enriched with one or more separation passes with water.

6. A method according to claim 1, wherein amino acids are obtained from industrial residue discharges from molasses processing.

7. A method according to claim 6 wherein an amino acid fraction obtained after said the first separation pass is concentrated and eluted again in a second separation pass with dilute or diluted solution of said starting material.

8. A method according to claim 6 wherein an amino acid fraction obtained is concentrated and, after said separation with said solution also eluted and enriched with one or more separation passes with water.

9. A method according to claim 1 wherein, prior to introduction into said separating column, said vinasse or residual molasses is pre-treated by the removal of calcium and magnesium salts.

10. A method according to claim 1, wherein during said separation pass the temperature is held in the range from 70° to 95° C.

11. A method according to claim 1, wherein concentrating of said dilute or diluted solution of said starting material is carried out with a concentration of 5% dry matter.

12. A method according to claim 1, wherein organic acids are obtained from industrial residue discharges from molasses processing.

13. A method according to claim 1, wherein pyrrolidone carboxylic acid is obtained from industrial residue discharges from molasses processing.

* * * * *